(12) United States Patent
Abrams et al.

(10) Patent No.: US 7,070,053 B1
(45) Date of Patent: Jul. 4, 2006

(54) SYSTEM, METHOD, AND APPARATUSES FOR MAINTAINING, TRACKING, TRANSPORTING AND IDENTIFYING THE INTEGRITY OF A DISPOSABLE SPECIMEN CONTAINER WITH A RE-USABLE TRANSPONDER

(75) Inventors: Robert Abrams, Albany, NY (US); Jean-Pierre Giraud, Paris (FR)

(73) Assignee: CV Holdings LLC, Amsterdam, NY (US)

( * ) Notice: Subject to any disclaimer, the term of this patent is extended or adjusted under 35 U.S.C. 154(b) by 477 days.

(21) Appl. No.: 10/140,698

(22) Filed: May 7, 2002

Related U.S. Application Data

(63) Continuation-in-part of application No. 09/947,596, filed on Sep. 5, 2001, now abandoned.

(60) Provisional application No. 60/229,917, filed on Sep. 5, 2000.

(51) Int. Cl.
*B65D 85/00* (2006.01)
*B65D 25/00* (2006.01)
*B01L 3/00* (2006.01)
*G01N 37/00* (2006.01)

(52) U.S. Cl. .............................. 206/459.5; 73/864.91; 220/527; 220/600; 235/375; 235/385; 422/102; 422/104

(58) Field of Classification Search .......... 422/99–105; 215/250, 253; 220/265, 503, 527, 600, 629; 600/573; 73/864.91; 604/224–226; 235/375, 235/385; 340/572.1; 206/459.5
See application file for complete search history.

(56) References Cited

U.S. PATENT DOCUMENTS

| | | | | |
|---|---|---|---|---|
| 4,418,702 A | * | 12/1983 | Brown et al. .............. 600/573 |
| 4,741,346 A | * | 5/1988 | Wong et al. ................ 600/573 |
| 4,783,056 A | * | 11/1988 | Abrams ...................... 264/238 |
| 4,925,630 A | * | 5/1990 | Grunwald ................... 422/104 |
| 5,012,941 A | * | 5/1991 | Abrams et al. ............. 215/250 |
| 5,133,470 A | | 7/1992 | Abrams et al. |
| 5,166,498 A | | 11/1992 | Neeley |
| 5,325,980 A | * | 7/1994 | Grimm et al. ............. 220/375 |
| 5,381,487 A | | 1/1995 | Shomos |
| 5,397,542 A | * | 3/1995 | Nelms et al. ............... 422/104 |
| 5,429,699 A | | 7/1995 | Abrams et al. |
| 5,513,768 A | | 5/1996 | Smith |
| 5,660,301 A | | 8/1997 | Kaplowitz |
| 5,777,303 A | | 7/1998 | Berney |
| 5,880,675 A | | 3/1999 | Trautner |
| 5,942,987 A | | 8/1999 | Heinrich et al. |
| 6,007,104 A | | 12/1999 | Draper |
| 6,083,462 A | * | 7/2000 | Ikonen et al. ............... 422/104 |
| 6,085,603 A | | 7/2000 | Riekkinen |
| 6,294,999 B1 | | 9/2001 | Yarin et al. |

(Continued)

FOREIGN PATENT DOCUMENTS

CA 2204201 11/1998

(Continued)

*Primary Examiner*—Bryon Gehman
(74) *Attorney, Agent, or Firm*—Greenberg Traurig

(57) ABSTRACT

A method of maintaining, tracking and identifying the integrity of a disposable specimen container comprising the steps of: writing to an RFID device attached to an individual specimen vial information including the date and a unique identification of the vial; putting sample in the specimen vial; writing to the RFID device attached to the specimen vial information including the time and the day; storing the vial in an environment to maintain its integrity; sending the vial to a laboratory for analysis; inventorying the vials by scanning the RFID attached to the individual vials; and separating the RFID device from the vial so that the RFID device may be re-used.

4 Claims, 4 Drawing Sheets

U.S. PATENT DOCUMENTS

| | | |
|---|---|---|
| 6,475,443 B1 | 11/2002 | Van Deursen et al. |
| 6,535,129 B1 | 3/2003 | Petrick |
| 6,652,812 B1 | 11/2003 | Vartiainen et al. |
| 6,796,670 B1 * | 9/2004 | Winters et al. ............... 362/34 |
| 2002/0076819 A1 | 6/2002 | Bowman et al. |

FOREIGN PATENT DOCUMENTS

| | | |
|---|---|---|
| DE | 196 21 179 | 11/1997 |
| WO | WO 01/79988 | 10/2001 |
| WO | WO 01/81823 | 11/2001 |

* cited by examiner

SYSTEM, METHOD, AND APPARATUSES FOR MAINTAINING, TRACKING, TRANSPORTING AND IDENTIFYING THE INTEGRITY OF A DISPOSABLE SPECIMEN CONTAINER WITH A RE-USABLE TRANSPONDER

STATEMENT OF RELATED APPLICATIONS

The present application is a continuation-in-part of U.S. patent application Ser. No. 09/947,596 filed Sep. 5, 2001, now abandoned, which application claims the benefit of the filing date of provisional U.S. patent application No. 60/229,917, filed Sep. 5, 2000, abandoned

FIELD OF THE INVENTION

The present invention is directed to the system, method, and apparatuses for maintaining, tracking, and identifying the integrity of a disposable specimen container with a re-usable transponder.

BACKGROUND OF THE INVENTION

Radio frequency identification (RFID) tags and radio frequency identification tag systems are used for identification and/or tracking of equipment or inventory such as pallets, trucks, dollies or boxes or even the whereabouts of some animals, such as livestock in certain situations. These RFID systems are radio communication systems in which communications is provided between a radio transceiver, or interrogator, and a number of small, identifying labels or tags. These tags are read while in the radiation pattern or field of the interrogator, which may be connected to a computer-based tracking system. The intent of an RFID system is to provide a reliable and secure architecture that meets a predetermined performance requirement, while minimizing the cost of the interrogator and the tags.

Conventionally, in the operation of RFID systems, the interrogator transmits to the tags using modulated radio signals, and the tags respond by transmitting modulated radio signals back to the interrogator. Specifically, the interrogator first transmits an amplitude-modulated signal to the tag. Next, the interrogator transmits a continuous-wave (CW) radio signal to the tag. The tag then modulates the CW signal using modulated back scattering (MBS) wherein the antenna is electrically switched, by the tag's modulating signal, from being an absorber of radio frequency (RF) radiation to being a reflector of RF radiation; thereby encoding the tag's information onto the CW radio signal. The interrogator demodulates the incoming modulated radio signal and decodes the tag's information message. A radio frequency identification tag system conveniently provides for reading the information from the radio frequency identification tag at a small distance using radio frequency (RF) data transmission technology. Typically, the user simply holds or places the radio frequency identification tag near a base station that transmits an excitation signal to the radio frequency identification tag powering circuitry contained on the radio frequency identification tag. The circuitry, responsive to the excitation signal, communicates the stored information from the radio frequency identification tag to the base station, which receives and decodes the information. In general, radio frequency identification tags are capable of retaining and, in operation, transmitting a substantial amount of information—sufficient information to uniquely identify individuals, packages, inventory and the like.

In one application that is relevant to the present invention, specimen containers (e.g. vials) are used conventionally in the dairy and the drug testing industries. In such industries, a unique specimen sample (e.g. milk in the dairy industry, and blood or urine in the drug testing industry) is maintained in the vial. The unique specimen must be identified and tracked. In some applications, the specimens are identified and tracked by a unique bar code. Bar codes are typically located using a hand held optical scanner. Such bar code labeling systems utilize a light beam emitted from the scanner to "read" the bar code label. These systems require a direct line of sight between the scanner and the bar-code label, thus greatly limiting their utility.

In addition, the specimen containers may be provided with access that can be gained only by producing visible evidence that the container has been opened whether by accident or on purpose (e.g. use of tape or seal). Such a container is useful in the transportation and storage of liquid specimens for example, to ensure the integrity, of the specimen. The integrity of the specimen in the vial is becoming increasingly important in the dairy industry and for drug testing. It is important to ensure the so-called "guaranteed chain of custody" of the container contents by providing a "tamper-evident" seal to the vial—to protect from being opened by unauthorized personnel who might tamper with the contents.

SUMMARY OF THE INVENTION

The present invention is a vial is provided with structure to house and retain an RFID tag. In yet another embodiment, the invention is a vial and RFID tag combination. The vial is intended for a single use, and then is disposed. The RFID tags are removed from the vial and reused as often as is possible.

The vial of the present invention can be, in its structure and design, a conventional vial with respect to its intended use, which for example could be a vial for holding a milk sample or a vial for holding a urine specimen, which then is provided with the structural attributes disclosed herein that enable it to house and retain an RFID tag. The vials of the present invention may be those vials disclosed in U.S. Pat. Nos. 5,012,941 and 5,133,470, both of which are incorporated herein by reference. These vial constructions would then be modified as disclosed herein in order to have the features that would allow the vials to receive and retain an RFID tag. Also, as disclosed in the patents incorporated herein by reference, the vials may be provided with a breakaway tab that breaks off the first time the vial is opened.

In one embodiment, the vial comprises a container portion having a bottom wall, an internal cavity, and sidewall. In one embodiment, the bottom wall is offset from the bottom of the sidewall. This arrangement defines a rim that extends from sidewall bottom to bottom wall.

A retaining ring, having a perimeter that fits within the perimeter of the rim, is joined to the bottom wall and extends in the direction of the sidewall bottom. The retaining ring has regions of a first smaller height dimension and lugs 20, which are regions of a second greater height dimension. Further, spacer elements are positioned at several locations around the inner wall of the retaining ring. The spacer elements may be positioned along the retaining ring in the regions of the first smaller height dimension, approximately halfway between the lugs. A depression is provided in the center of the bottom wall.

To secure the RFID tag, it is placed within the retaining ring. The lugs are then reconfigured, that is, moved out of the substantially vertical state to a state that is at least partially horizontal, in which the lugs extend over the tag in order to secure it in place. Any technique that imparts sufficient energy to the plastic vial in order to soften the lugs, so that they can be bent over the RFID tag, can be employed. Ultrasonic energy may be employed for this task. Alternatively, energy from a heat source may also be applied.

The vials can be constructed of plastic materials such as polypropylene and polyethylene. The plastic materials that are employed should not be adversely affected by a sterilizing dose of gamma radiation.

In yet another embodiment, a notch is cut out of the rim. The notch is employed to properly orient the vial during opening.

In another embodiment, the invention is a puck that is used to escort the vial assembly along the conveyor system. The puck has a cavity positioned within the surrounding sidewalls. The cavity is sized maintain the vial in an upright position. That is, it is dimensioned so that the outer surface of the vial contacts the inner wall of the cavity and/or is in close proximity thereto. In a further embodiment, the puck is provided with a bottom surface and cavity-defining sidewalls that extend upward from the bottom surface. The puck may be provided with openings positioned in the sidewalls, in the bottom surface, or in both locations. Furthermore, the puck may be provided with a structural attribute that, in cooperation with a structural attribute of the vial assembly, aligns and orients the vial, so that the vial is properly positioned at the time it visits the stations along the path where testing is conducted. For example, a notch can be located at the bottom of the vial, and the puck can be provided with a feature that mates with the notch. This arrangement can be used to insure that the vial is properly aligned for its visit to the lid opening station, thereby optimizing the number of vials successfully opened by automated equipment.

DETAILED DESCRIPTION OF THE INVENTION

Figure 2:
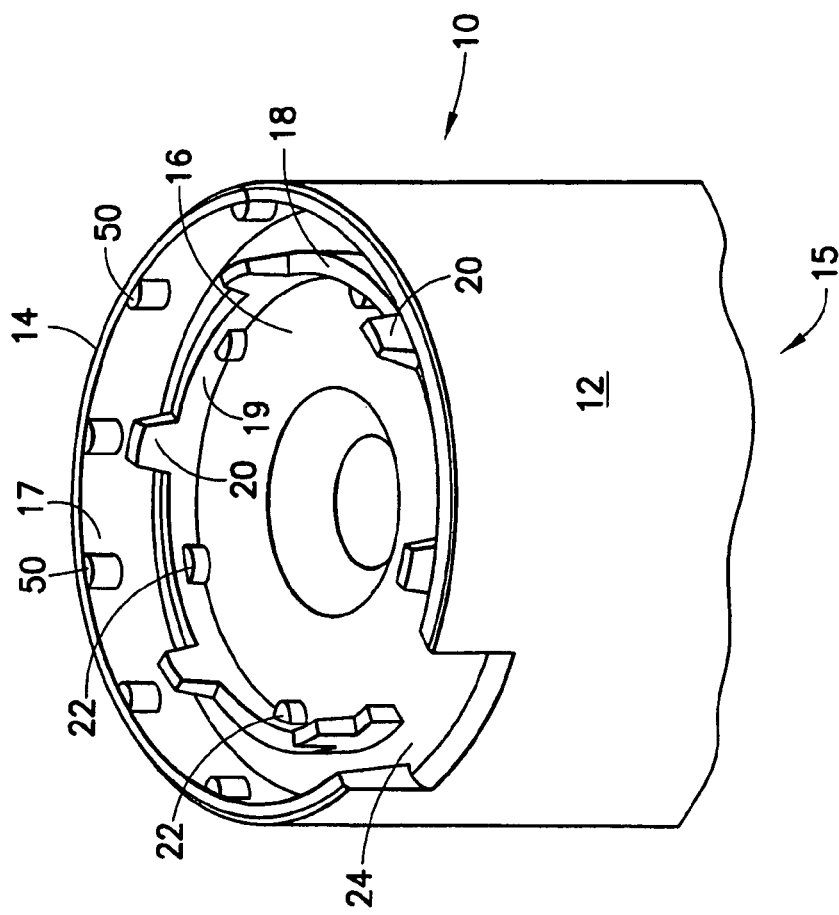
FIG. 2 is a perspective view of an embodiment of the present invention, with the RFID tag absent.
Figure 1:
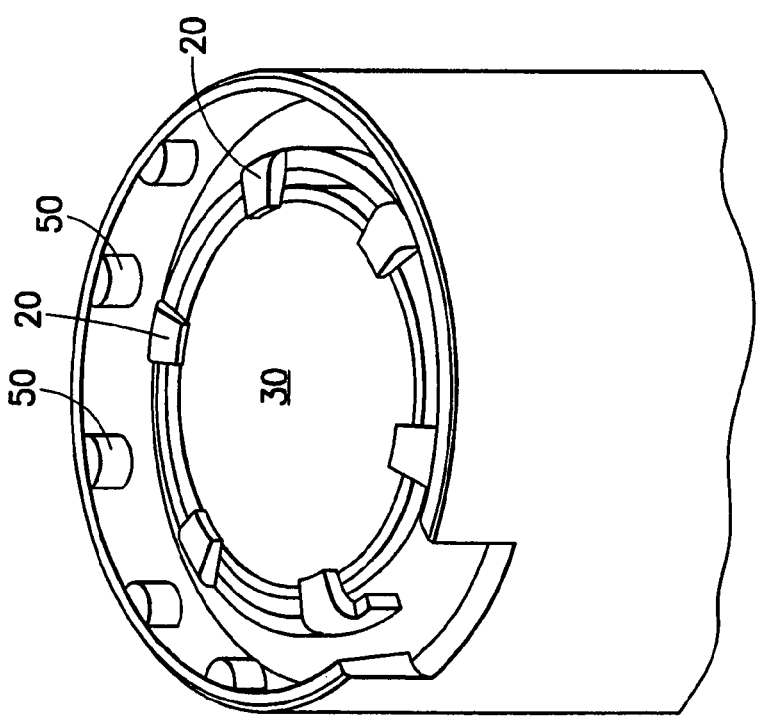
FIG. 1 is a perspective view of an embodiment of the present invention, with the RFID tag present.

The vial of the present invention can be, in its structure and design, a conventional vial with respect to its intended use, which for example could be a vial for holding a milk sample or a vial for holding a urine specimen, which then is provided with the structural attributes disclosed herein that enable it to retain an RFID tag. The vials of the present invention may be those vials disclosed in U.S. Pat. Nos. 5,012,941 and 5,133,470, both of which are incorporated herein by reference. These vial constructions would then be modified as disclosed herein in order to have the features that would allow the vials to receive and retain an RFID tag. Also, as disclosed in the patents incorporated herein by reference, the vials may be provided with a breakaway tab that breaks off the first time the vial is opened. As shown in FIGS. 1 and 2, the vial comprises a container portion 10 having a bottom wall 16, an internal cavity 15, and sidewall 12. The bottom wall 16 is offset from the bottom 14 of the sidewall 12. This arrangement defines a rim 17 having a length dimension that extends from sidewall bottom 14 to bottom wall 16.

A retaining ring 18 has a perimeter positioned within the perimeter of the rim 17. The retaining ring 18 is joined to the bottom wall 16 and extends for at least a portion of the length dimension of the rim 17, in the direction of sidewall bottom 14. The retaining ring has regions of a first smaller length dimension 19 and lugs 20, which are regions of a second greater length dimension. Spacer elements 22 are positioned at several locations around the inner wall 23 of the retaining ring. The spacer elements may be positioned along the retaining ring 20 in the regions of the first smaller height dimension 19, approximately halfway between the lugs 20. A depression is provided in the center of the bottom wall 16.

The rim is further provided with a number of ribs 50, that extend inward. The ribs are positioned around the perimeter of the rim 17.

Figure 9:
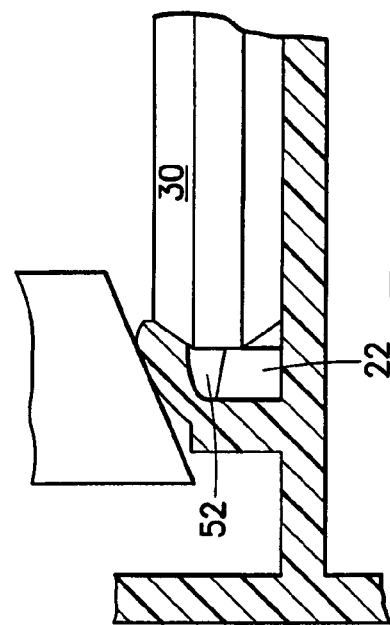
FIG. 9 is a perspective view showing the manner in which the lugs can be shapen over the RFID tag.

To secure the RFID tag 30, it is placed within the retaining ring. The lugs 20 are then bent down and in over the tag to secure it in place. Any technique that imparts sufficient energy to the plastic vial in order to soften the lugs, so that they can be bent over the RFID tag, can be employed. In one example, ultrasonic energy may be employed for this task. FIG. 9 demonstrates an arrangement by which the lugs 20 can be reconfigured in order to extend over the RFID tag and retain it in place. Ultrasonic devices that can be used to reshape the lugs are available from Branson Ultrasonics Corporation, Danbury Conn. USA.

Alternatively, energy from a heat source may also be applied. A mechanism that applies pressure to the lugs when they are in the softened state can be employed to effect the bending of the lugs. The mechanism may have a bar or plate or the like that effects bending from the original, substantially vertical state of the lugs, to the final bent state in which the lugs are at least partially horizontal. This component may be employed to retain the lugs in the bent state until after the plastic cools, at which time the lugs will remain in the bent state after pressure is removed.

The vials can be constructed of plastic materials such as polypropylene and polyethylene. The plastic materials that are employed should not be adversely affected by a sterilizing dose of gamma radiation.

In yet another embodiment, a notch 24 is cut out of the rim 17. The automated equipment that opens the vials prior to drawing a sample employs the notch in order to properly orient the vial, to insure that the vial is correctly opened. The vial should have a diameter large that is large enough so that the vial can hold an RFID tag (e.g. a 22 mm diameter tag, a 17 mm square tag). Consequently, these dimensions set the size required for the retaining ring. While the arrangement shown in the Figures shows a circular tag, it should be readily understood that the person of skill in the art could modify the embodiments shown herein to provide the necessary adaptations for any other shaped tag (e.g. square tag).

The lugs that hold the RFID tags should be designed to be strong enough to withstand one complete use cycle. Merely by way of example, with regard to a milk sample, this includes travel to and from and processing at the following locations: the tag insertion station, the transport rack, the milk tanker cool box, the milk tanker RFID read/write station, the transport racks, the laboratory automation, and the tag removal station.

One advantage of the structure disclosed herein is that the lugs provide evidence of tampering, or the lack thereof. That is, observation of the lugs will provide visual indication on whether they have been tampered with.

As detailed below, the vials of the present invention can be formed in the mold. The retaining ring, spacers, rim and other features described above can also be formed in the mold by these same molding techniques.

In another aspect, the present invention generally relates to a method of maintaining, tracking and identifying the integrity of a specimen container using a disposable specimen container and a reusable RFID tag.

Suitable RFID devices include a read-only or a read/write transponder. For a read/write RFID device, the transponder acts as a both a storage device and a display device. Examples of RFID devices suitable for the present invention include: (a) the "RI-TRP," "RI-101," "RI-102," and "RI-103" models from Texas Instruments; and (b) the "Gem-Wave Ario" and the "GemFly" models from Gemplus. The specific transponder may be chosen based on the specific application including: (a) the size and shape of the container and thus, the maximum surface area that is available for the transponder; (b) the environment (humidity, hazards and degree of special handling); (c) the need to re-use the transponder; (d) the memory capacity; (e) the size of the antenna; and (f) the cost. It is understood that the RFID device of the present invention includes any equivalent device that has the capability of both reading and writing such as the category referred to as "transponders."

For the dairy industry, the following is one embodiment of the method of the present invention:
  (a) a disposable vial and RFID tag combination that are assembled as described above;
  (b) information including the date and a unique identification of the vial is written to the RFID device attached to the individual specimen vial;
  (c) the vials are sent to the dairy (and/or given to a tank driver);
  (d) when the milk is pumped from a specific tank at the dairy to the tanker truck, a milk sample is taken (either automatically or manually) and is put in the specimen vial;
  (e) information including the specific dairy, the specific dairy tank, the time, the day and/or the temperature of the milk are written to the RFID device attached to the specimen vial;
  (f) the vial is then stored in an environment to maintain its integrity (e.g. insulated container, refrigerator unit);
  (g) the vial(s) are sent to a laboratory for analysis;
  (h) at the laboratory, the vials are inventoried by scanning the RFIDs attached to the individual vials;
  (i) at the laboratory, information including the routing (e.g. test required such as fat/protein/bacteria/antibiotics analysis) of the sample is written to the RFID attached to the individual specimen vial; and
  (j) the RFID device is separated from the vial so that the RFID device may be re-used and the corresponding vial is ground-up so that the plastic may be recycled.

Steps (a) and (b) can be effected by an automated process that is practiced at the site where the RFID tag is joined to the vial. Steps (d) and (e) take place at the dairy. The information mentioned in step (e) may be written to the tag by employing a hand held device, after first inputting the necessary information on a keypad or other device. Steps (h), (i), and possibly (j) occur at the testing laboratory. Steps (h) and (i) may occur along the automated assembly line, and information read from the vials can be employed to determine and assign the ultimate destination of the vial, such as the test station for nutritional analysis. Alternatively, at a given location on the conveyor, information may be written to the tag, which is used further on down the conveyor to assess and determine the ultimate destination of the vial. A series of RFID reader and writer devices are provided on the conveyor system in order to read and write information from and to the RFID tags.

While step (j) can occur at the laboratory, it may also occur at a remote location, which may include the location where steps (a) and (b) take place. Removal of the RFID tags may be an automated process step.

In a more specific embodiment of the above-described method, a hand-held scanner may be used to either write information to and/or read information from the RFID device. For example, the tank driver and/or the dairy may use the hand-held scanner to read/write information including: (a) the date and a unique identification to the RFID device attached to the individual specimen vial; and (b) when the milk is pumped from a specific tank at the dairy to the tanker truck, the specific dairy, the specific dairy tank, and/or the temperature of the milk to the RFID device attached to the specimen vial. In another example, the laboratory personnel may use the hand-held scanner to read/write information including: (a) an inventory of the individual vials by reading the unique identification corresponding to the vial; and/or (b) routing information (e.g. test required such as fat/protein/bacteria/antibiotics analysis) of the sample by writing to the RFID device attached to the individual specimen vial. In another embodiment, the RFID device attached to the vial may be scanned without requiring a direct line of sight between the scanner and the RFID device. In this way, the vials contained within the larger containers do not need to be taken out and individually scanned.

For the drug testing industry, the following is one embodiment of the method of the present invention:
  (a) a disposable vial and RFID tag combination that are assembled as described above;
  (b) information including the date and a unique identification of the vial is written to the RFID device attached to the individual specimen vial;
  (c) the vials are sent to the office (e.g. physicians office, testing laboratory) where the patients urine or blood specimen is obtained;
  (d) when the patient's blood or urine specimen is obtained, the specimen is put in the specimen vial;
  (e) information including the individual's identification, the time, the day and/or additional office information are written to the RFID device attached to the specimen vial;
  (f) the vial(s) are sent to a laboratory for analysis;
  (g) at the laboratory, the vials are inventoried by scanning the RFIDs attached to the individual vials;

(h) at the laboratory, information including the routing (e.g. test required such as the type of drug to be tested for) of the sample is written to the RFID attached to the individual specimen vial; and (i) after all testing is complete and the specimen is no longer needed, the RFID device is separated from the vial so that the RFID device may be re-used and the corresponding vial is ground-up so that the plastic may be recycled.

In yet a further embodiment of the present invention, the routing step may be automated so a conveyor-like system is designed where the vials are automatically routed to the proper station based on a scanner reading the individual RFID devices attached to each vial.

Figure 3:
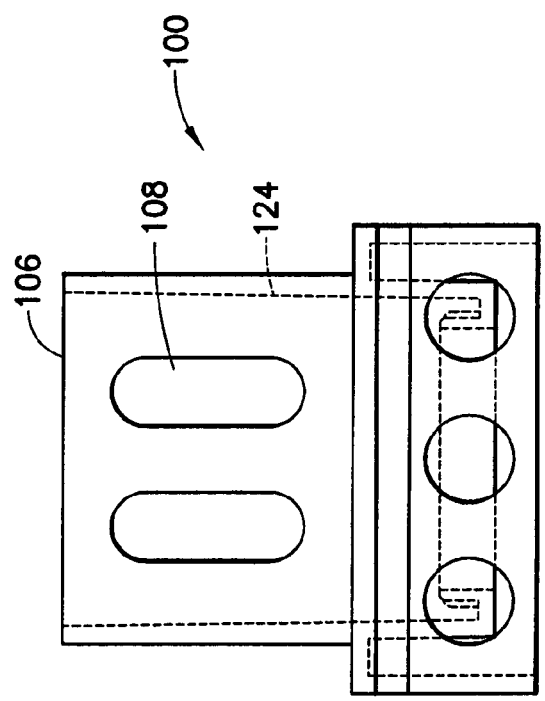
FIG. 3 is a side elevational view of an embodiment of a puck.
Figure 6:
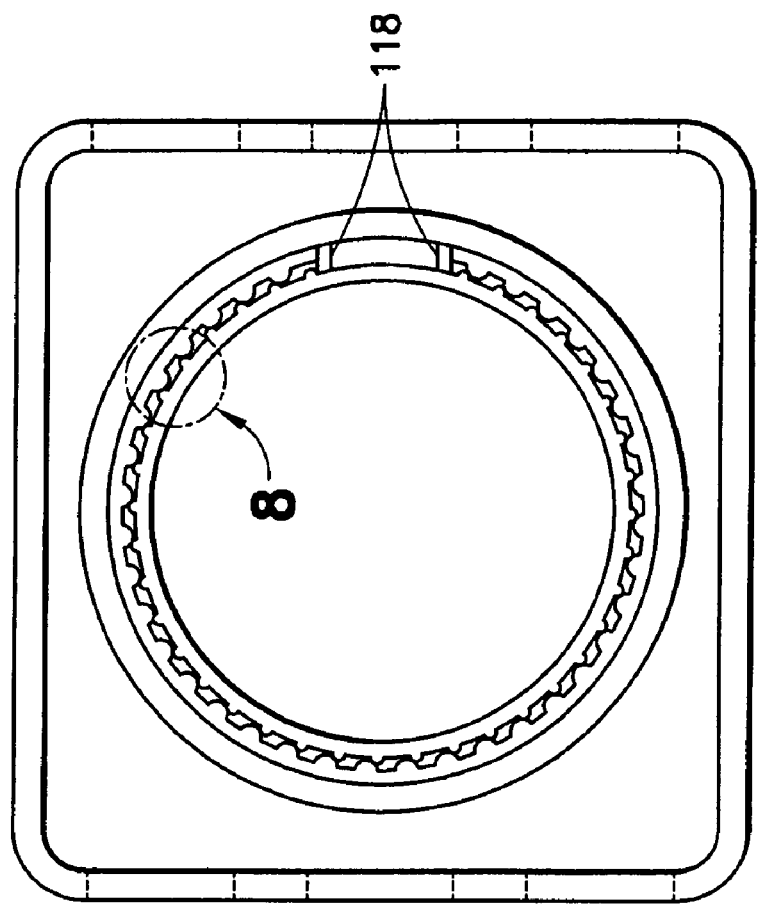
FIG. 6 is a top view showing, in cross section, the bottom of the vial and puck while the former is retained in the latter.

In yet another embodiment, the invention is a puck that escorts the vial around the assembly lines described above for milk testing and drug testing operations. FIGS. 3–8 show a puck 100, both alone and with a vial 10 disposed inside of it. FIG. 3 shows the exterior of the puck, having a base portion 102 of greater cross section than the elevated portion 104 that rises above it. The base portion and the elevated portion form the sidewalls of a cavity 106 in which the vial 10 resides. Both the base portion and the elevated portion are provided with through-holes 108, that, among other things, permit water to freely circulate over the surface of the vial. In some instances, it may be desirable to flow warm or hot water over the vials while they reside in the pucks.

Figure 4:
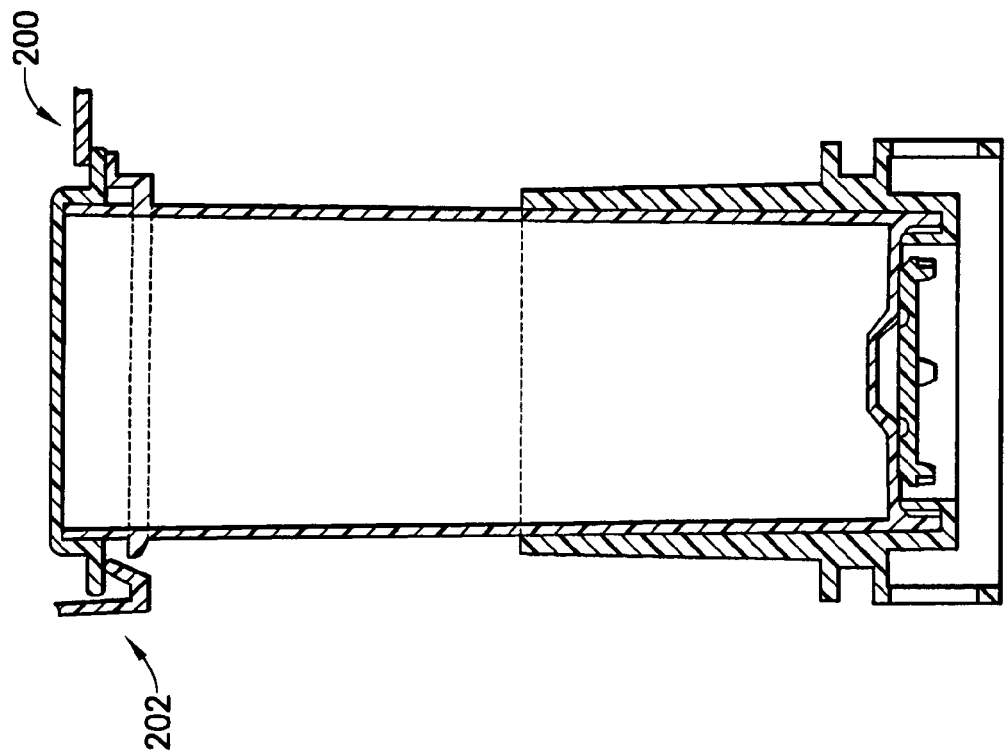
FIG. 4 is side elevational view showing a vial retained in a puck.
Figure 5:
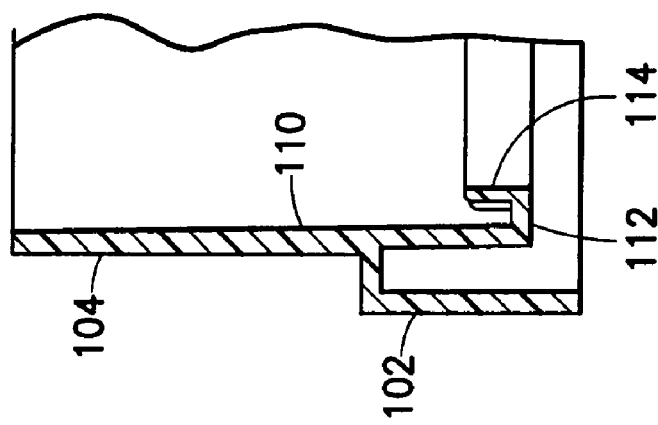
FIG. 5 is cross sectional views of the walls of the vial and puck while the former is retained in the latter.
Figure 8:
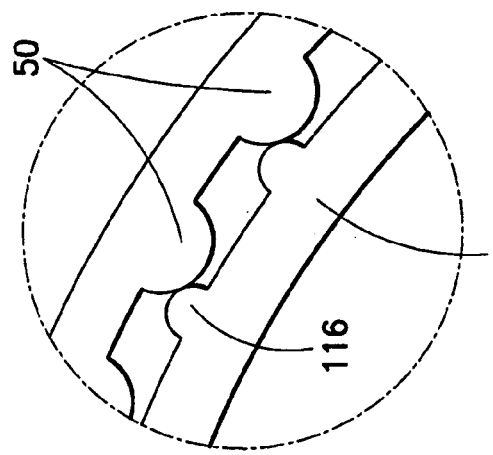
FIG. 8 is a perspective view showing the engagement between the puck and vial.

As shown in FIGS. 4 and 5, the bottom region 112 of puck sidewall 110 is provided with an upward-turned hook 114 that grasps the rim 17 of the vial 10. The bottom region 112 of puck sidewall 110 is further provided with a number of ribs 116. Ribs 116 are provided on the puck 100. The ribs 116 extend into the space between the bottom region 112 and the hook 114. The ribs 116 of the puck 100 are positioned around the bottom region, at the place where the hook 114 and bottom region 112 come together. When the vial 10 is placed within the puck 100, the ribs 116 of the puck 100 engage with ribs 50 on the rim 17 of the vial 10. The ribs 116 of the puck and the ribs 50 on the rim 17 of the vial 10 form a frictional engagement, which aids in retaining the vial in place.

Figure 7:
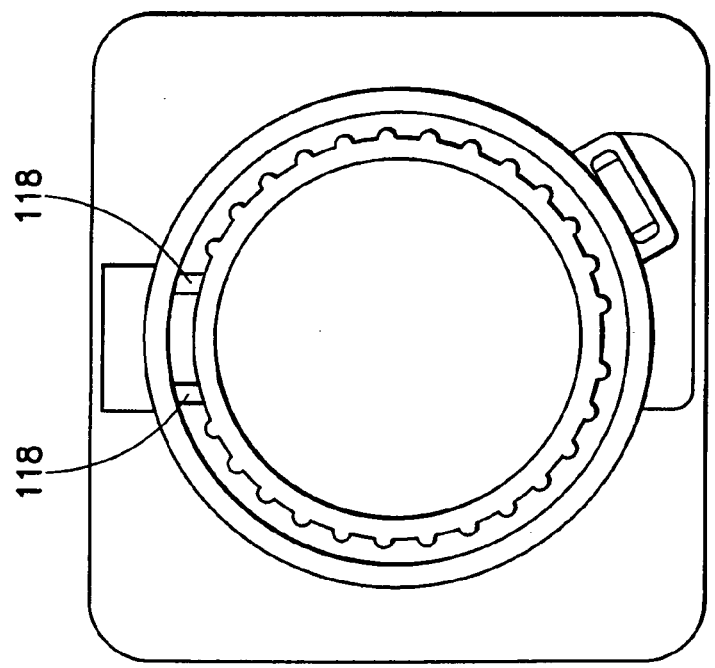
FIG. 7 is a top view showing, in cross section, the bottom and top of the vial and puck while the former is retained in the latter.

As best seen in FIG. 7, the puck is provided with bars 118 that are spaced apart from each other. The bars 118 are positioned to extend into the notch 24 on the vial 10 when the vial 10 is placed in the puck 100. Having the bars extend into the notch insure that the vial is properly oriented. The bars 118 engage the inner surface of the notch 24 that is provided in the rim 17 of the vial 10. The bars 118 orient the vial 10 so that it is properly aligned for certain procedures that are undertaken along the conveyor, such as the automated opening of the vial lid.

The pucks may be constructed of a strong durable material, such as a polyamide. In some embodiments, the polyamide may be metal-filled in order to modify the heat transfer properties of the polymer.

The automated opening of the lid may be accomplished in the following manner. As just described, the properly oriented vial will enter the lid opening station. A retaining element 200 (see FIG. 4) will contact the hinge that joins the lid to the container portion of the vial, applying a downward force on the hinge. A hook 202 will then approach the tab on the front portion of the lid and contact the tab on the underside thereof. The hook will then be moved upward, which applies an upward force to the lid and thereby opens the vial. The pucks facilitate the movement of the vial along conveyor systems, and where necessary, maintain the vial in an upright position. Examples of various stations along the conveyor, when the puck may aid the transport and orientation of the vial, include: (a) sample heating stations; (b) mixing stations; (c) maintaining orientation of the vial for through a station or stations for automated venting, opening and closing of the lid.

The pucks are sized at their base with dimensions sufficient to confer stability to the vial, yet small enough to minimize the space requirement in the buffer and storage areas. That is, the puck remains stable while it is being moved around by the conveyor system.

The puck can be any shape, however, to maintain orientation, it may be preferable to provide shapes that will avoid rotational movement while moving along the conveyor, such as non-circular shapes. Squares may be well suited for the shape of the puck.

Vials situated in pucks will arrive at the tag removal station. It may be desirable to remove the tags while the vial is still in the puck. To this end, a hole in the bottom of the puck may be provided. The hole should be large enough to accommodate a tag removal tool and permit the removal of the tag. As shown in FIG. 9, a gap 52 is present between the spacer and the lug. During removal of the RFID tag, the cutting blade that is employed to cut the lugs will move completely through the lugs and extend into the gap, insuring that the lugs are completely severed. During the cutting operation, the vial may be partially rotated, possibly within the range of 10°–15°, or as required by the dimensions of the lugs, to aid in the severing operation.

A sidewall of approximately 1 or 2 mm around the circumference of the base should be sufficient to locate and retain the vial.

At various points in the automated system, the samples (and pucks) will be heated to 40° C. in sample heating stations. The sample heating stations may move the pucks along X-Y coordinates in a heating station, while the samples are sprayed with hot water. Likewise, since the vials circulate in a milk-testing environment, where there is bound to be spillage, it may be desirable to clean them in a dedicated cleaning station—using hot water and optionally, an anti-bacterial agent. Providing openings in the puck will maximize contact between the fluid and the vial.

In a further embodiment of the RFID device, radio frequency identification tag is formed by directly joining a radio frequency identification tag circuit chip ("circuit chip") to an article having an integrally formed antenna. Article may be a substrate formed from a sheet of material. The substrate may be the specimen container. Moreover, the substrate material may be any suitable material for the particular application such as paper, plastic (including polyester and metalized polyester material), synthetic paper, reinforced paper, cardboard, coated cardboard and the like.

In one embodiment, the RFID tag is attached to the container, which identifies the container and thus the customer. For example, this tag may be secured to any part of the container including the lid, the bottom, the side or the top of the container. As such, the vial may be specifically designed to accommodate the RFID device. Such a tag may include a relatively flat or thin coil connected to an integrated circuit (IC) disposed within the confines of the coil. Thus, the coil of RFID tag is disposed substantially in a horizontal plane within the lid.

The apparatus and process of the present invention may be used with a variety of bodies including bottles, vials, spouts or any other containers. Although the examples describe a vial, the invention covers any type of container that may be used to transport specimen samples. The invention is described in the description with respect to a vial.

In another embodiment, the vial may be cylindrical in shape with an integrally formed bottom. A cap may be provided which is adapted to seal the vial closed with a substantially hermetic seal. The cap may be integrally connected to the vial with a small flange. The vial and cap may be injection molded in the mold from a thermoplastic material. Examples of processes of making such vial and of designs for such vials are disclosed in U.S. Pat. Nos. 4,812,116, 4,783,056, 5,723,085, and 6,303,064 that are incorporated by reference herein.

In a further embodiment, vials of the type to which the present invention relates are generally injection-molded plastic vials that have caps adapted to seal the vial closed with a substantially hermetic seal. The cap may or may not be integrally connected to the vial, but is preferably joined thereto with a small flange. It is important to maintain the sterility of the interior of the vial prior to use. Accordingly, in order to maintain the sterility of the interior of the vial the cap must be closed onto the vial while the vial is in an aseptic environment.

In a further embodiment of the present invention, the vial is designed so that the RFID device is sufficiently secured to the vial so that the RFID device remains attached to the vial during regular shipping and handling. Such a securing device may include, but are not limited to, a clip-on system, a slotted system, and snap-on system. At the same time, the securing device is designed so that, after the specimen has been tested, the RFID device may be intentionally removed from the vial with out incurring damage to the RFID device. In this way, the RFID device may be re-used while the corresponding vial is ground-up and the plastic material may be recycled. The present invention takes advantage of the ability to dispose of the vial after each use so as to maintain integrity and sterility of the specimen sample while, at the same time, to re-use the RFID device. Consequently, the present invention is environmentally "green"—the vial may be recycled and the plastic re-used and the RFID device may be continually re-used. In one embodiment, an automatic system may be designed where the RFID is automatically removed from a used vial and is inserted in a new vial while the used vial is ground-up and prepared for recycling. One process of automatically recycling the vial is disclosed in U.S. Pat. No. 5,979,804, which is incorporated by reference herein.

In another aspect of the present invention, the vial may be a tamper-proof container and cap for indicating whether the container has been opened during transport to or from a specimen-receiving site. For example, one or more destructible connections are provided between the container and cap, that connection including one or more destructible members which hold the cap in a closed condition whereby the cap can be opened only in response to the destruction of the destructible member. Accordingly, an opening of the closed container during transport thereof to a specimen-receiving site (e.g. a laboratory) is evident from a destruction of the destructible member. One embodiment of such a tamper-proof design is described in U.S. Pat. No. 5,012,941, which is incorporated by reference herein.

In yet another aspect of the present invention, the device that secures the RFID device to the vial may be a tamper-proof design for indicating whether the RFID device has been either replaced with another RFID device or has been tampered with during transport to or from a specimen-receiving site and/or during handling. For example, one or more destructible connections may be provided between the RFID device and container, that connection including one or more destructible members which hold the RFID device to the container whereby the RFID device can be removed from the container only in response to the destruction of the destructible member. Accordingly, tampering with the RFID device during transport and/or handling thereof to a specimen-receiving site (e.g. a laboratory) is evident from a destruction of the destructible member.

We claim:

1. A container comprising a disposable vial and a cap, wherein a bottom surface of the vial is recessed from a bottom end of a vial sidewall, the bottom surface comprised of:
    a ring depending from the bottom surface in a direction away from the bottom surface to a first height dimension;
    a plurality of lugs, which are integral with the ring, extending from the ring in a direction further away from the bottom surface to a second height dimension greater than the first height dimension;
    wherein a space is defined inside the ring in which a RFID tag can be positioned, and wherein the lugs can be fixed into a position in which they extend over the tag when the tag is positioned in the space.

2. The container of claim 1 wherein the bottom surface is offset from the bottom end of the vial by a rim.

3. The container of claim 2, further comprising a notch located in the rim of the vial.

4. The container of claim 3 wherein the rim is provided with a plurality of ribs.

* * * * *